Jan. 29, 1952 H. D. GREPKE Plant Pat. 1,069
SPIREA PLANT
Filed July 18, 1950
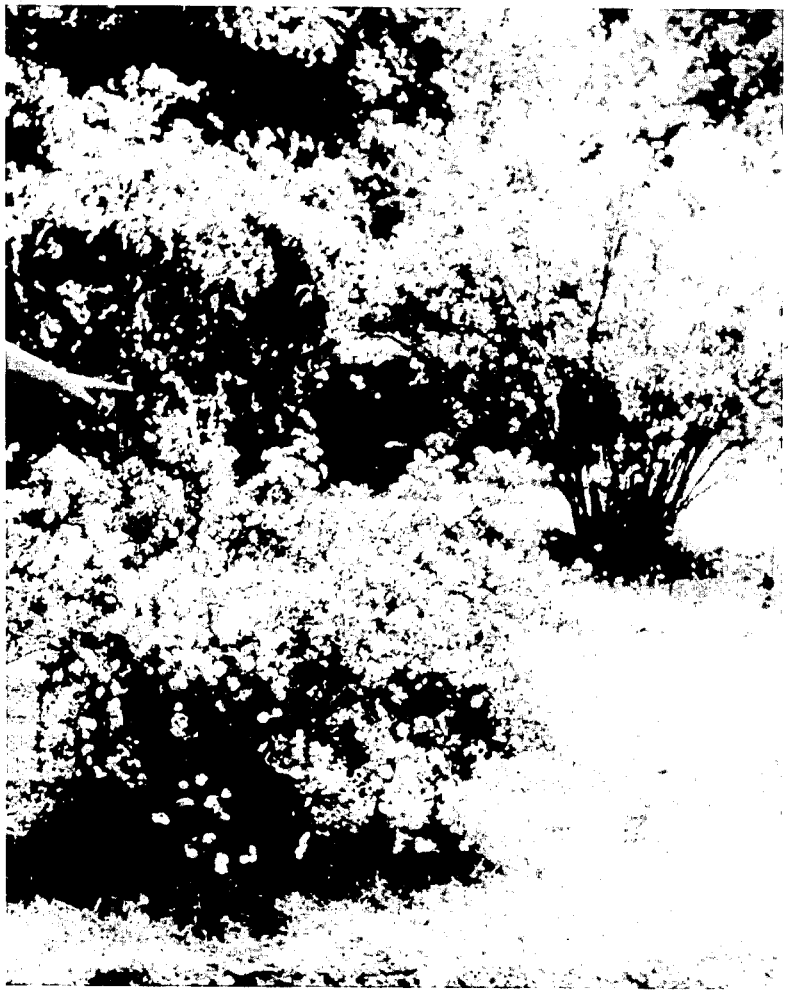
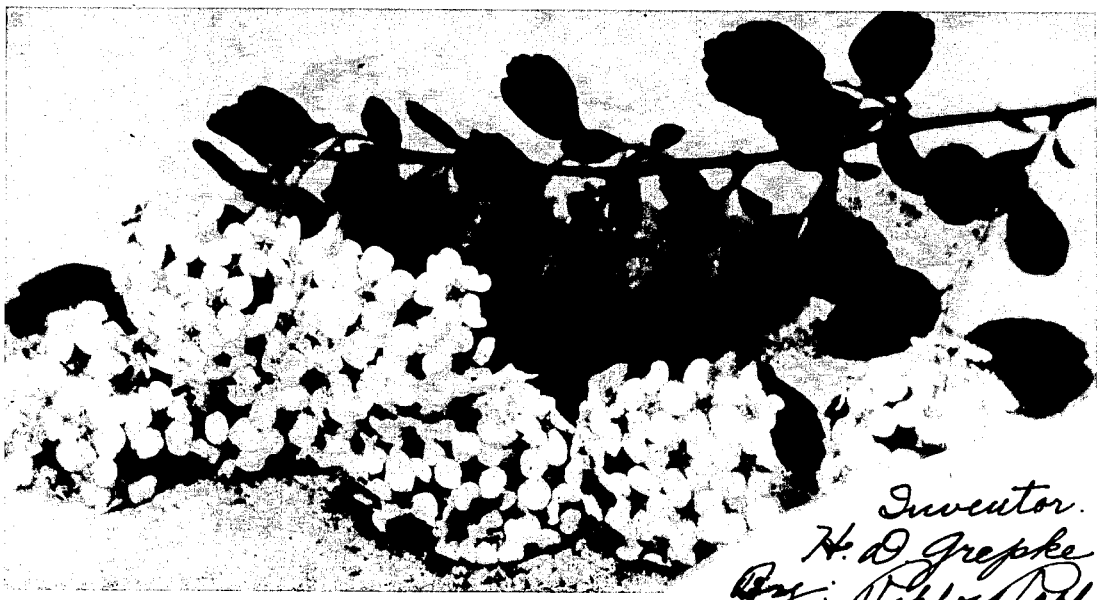
Inventor.
H. D. Grepke
By: Robb & Robb
attorneys.

Patented Jan. 29, 1952

Plant Pat. 1,069

UNITED STATES PATENT OFFICE 1,069

SPIREA PLANT

Henry D. Grepke, Fort Wayne, Ind., assignor to Stark Bro's Nurseries and Orchards Company, Louisiana, Mo., a corporation of Missouri Application July 18, 1950, Serial No. 174,555

1 Claim. (Cl. 47—59)

The present invention relates to a new and distinct variety of spirea plant, originating as a cultivated seedling of the variety "Spirea Van Houtte," said seedling resulting from seed planted by me on my cultivated property in Fort Wayne, Indiana.

The origin of this new variety will now be explained in more detail. During the growing of some plants of the variety "Spirea Van Houtte" on my property, and while looking over these plants on an occasion late in the summer season, I noticed one where the flower clusters had not all withered in the same manner. On this particular plant, there were clusters which had dried upright and which had retained their shape. Closer inspection and investigation showed these clusters to have tiny seed pods. Thereupon I became fascinated with the idea of growing spirea from seed. Accordingly, I collected all of the pods I could find and crushed these in the palm of my hand, but try as I would, I could not distinguish the seed from the chaff under the naked eye, although I later found this to be possible with the aid of a magnifying glass. Being originally unable to separate the seed from the chaff, I decided to plant the chaff and all, and in planting the same, I selected a nasturtium bed which was then under cultivation on my property, and sowed the seed and chaff among the nasturtium plants. However, despite careful and continuous observation of the bed through the following autumn, the spirea seed did not appear to grow, and the bed became matted with falling leaves which remained on the bed until I removed the same the following spring. After raking and cleaning the bed the following spring, I did not replant it, with the result that the bed grew up in weeds which were too tall to cut by a mower. Consequently, I was obliged to use a hand sickle to cut down the weeds later, and during this operation, I found the original seedling spirea which had obviously grown from the seed which I planted the previous year. While the plant was only several inches high, I was able to recognize it by the leaves, and I promptly removed the plant and transplanted it among other stock to protect it from harm. Thereafter, it was kept under careful and continuous observation over several years, during the course of which I found that the new seedling possessed characteristics which distinguished it from all other varieties of spirea, including its parent "Spirea Van Houtte," these novel characteristics having become fixed and fully established and later found to be transmissible by asexual reproduction, as will hereinafter more fully appear.

The new variety is characterized as a dwarf and otherwise is substantially identical in appearance with "Spirea Van Houtte" except that the leaves of the new variety are somewhat smaller in size than those of "Spirea Van Houtte," and the plants of the new variety are considerably smaller in size. In respect to vigor, hardiness, profusion of bloom, color and size of the blooms, the new variety is practically identical with "Spirea Van Houtte."

The dwarf size of the plants of the new variety is an important characteristic by reason of the fact that it may be availed of to great advantage in many landscape plantings around homes and other buildings, without overgrowing the windows, especially in the case of modern "ranch type" homes where the windows are relatively low.

By way of comparison with "Spirea Van Houtte" when grown under comparable conditions within a few feet of plants of the new variety, the plants of "Spirea Van Houtte" attained a height of six feet, while full grown plants of the new variety grew only thirty inches in height.

Asexual reproduction of the new variety by hard wood cuttings at Louisiana, Missouri, shows that the foregoing characteristics come true to form and are established and transmitted through succeeding propagations.

The accompanying drawing shows a specimen full-grown plant of the new variety and illustrates its relatively low height as represented by the yardstick shown in association with the plant, as well as in relation to plants of the same age of the parent variety which appear in the background; also an enlarged view of specimens of the foliage and blooms of the new variety.

The following is a detailed description of the new variety, with color terminology in accordance with Horticultural Color Guide:

Parentage: Seedling of variety "Spirea Van Houtte" (unpatented).

*Plant*

(Observations made from specimen plants grown at Fort Wayne, Indiana.)

Growth: Medium vigorous; dwarfed; spreading and arching; height 30 inches when full grown.

Branches: Spreading; arching; slender.

Leaves:

*Shape.*—Rhombic obovate; narrowed at base; incised serrate.

*Size.*—½ to ¾ inch x $\frac{3}{16}$ to $\frac{5}{16}$ inch.

*Color.*—Upper surface—Spinach Green, Color No. 0960, page 2, vol. 2; lower surface—Spinach Green, Color No. 0960/2, page 6, vol. 2.

Disease resistance: Good.

Insect resistance: Good.

*Flowers*

Borne: In many flowered umbels 1 to 1⅛ inch in diameter.

Color: White.

Date of bloom: May 22 to May 31.

Sepals: Spreading.

I claim:

A new and distinct variety of spirea plant, characterized as to novelty by its similarity in appearance to the variety "Spirea Van Houtte" (unpatented) and in respect to vigor, hardiness, profusion of bloom, color, size and date of bloom, but distinguished from "Spirea Van Houtte" by its somewhat smaller foliage and by its dwarf habit of growth, substantially as shown and described.

HENRY D. GREPKE.

No references cited.